United States Patent [19]
Moulton et al.

[11] Patent Number: 6,086,563
[45] Date of Patent: Jul. 11, 2000

[54] NEEDLE RETRACTION MECHANISM WITH PUSH START RETRACTION

[75] Inventors: William G. Moulton; Greg L. Brimhall, both of West Jordan, Utah

[73] Assignee: Becton, Dickinson and Company, Franklin Lakes, N.J.

[21] Appl. No.: 09/229,289

[22] Filed: Jan. 13, 1999

[51] Int. Cl.[7] .................................................. A61M 5/00
[52] U.S. Cl. ..................... 604/164.01; 604/198
[58] Field of Search ................... 604/198, 164, 604/165, 187, 192, 195

[56] References Cited

U.S. PATENT DOCUMENTS

| | | | |
|---|---|---|---|
| 4,747,831 | 5/1988 | Kulli | 604/110 |
| 4,772,265 | 9/1988 | Walter | 604/164 |
| 4,828,548 | 5/1989 | Walter | 604/164 |
| 5,125,414 | 6/1992 | Dysarz | 128/763 |
| 5,129,884 | 7/1992 | Dysarz | 604/164 |
| 5,480,385 | 1/1996 | Thorne et al. | 604/110 |
| 5,487,734 | 1/1996 | Thorne et al. | 604/195 |
| 5,542,927 | 8/1996 | Thorne et al. | 604/110 |
| 5,549,708 | 8/1996 | Thorne et al. | 604/110 |
| 5,616,135 | 4/1997 | Thorne et al. | 604/192 |
| 5,656,031 | 8/1997 | Thorne et al. | 604/110 |
| 5,836,917 | 11/1998 | Thorne et al. | 604/164 |

FOREIGN PATENT DOCUMENTS 9-28811  2/1997  Japan .

Primary Examiner—John D. Yasko
Attorney, Agent, or Firm—Eric M. Lee

[57] ABSTRACT

A needle retraction mechanism includes a hollow handle defining a cavity, a tab associated with the handle, a needle hub assembly movably disposed in the handle, a biasing mechanism to move the needle hub assembly from an extended position to a retracted position and an arm to hold needle hub assembly in the extended position against the bias of the biasing mechanism. The tab and arm are configured such that downward movement of the tab engages the arm to allow the needle hub to move to the proximal end of the handle. In addition, the tab and arm are configured so that at least a portion of the downward movement of the tab is translated into a proximally directed axial movement of the needle hub This facilitates movement of the needle hub and overcomes any static friction between the needle hub and the inner wall of the handle tending to hold the needle hub in the extended position.

8 Claims, 10 Drawing Sheets

NEEDLE RETRACTION MECHANISM WITH PUSH START RETRACTION

BACKGROUND OF THE INVENTION

This invention generally relates to needle retraction mechanisms. More particularly, this invention relates to needle retraction mechanisms that are used in the medical field. Such needle retraction mechanisms find particular applicability in connection with intravascular catheters, syringes, blood collection tubes and lancets.

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and are on the order of about one and one-half inches in length. The most common type of IV catheter is an over the needle peripheral IV catheter. As its name implies, an over the needle catheter is mounted over an introducer needle having a sharp distal tip. The catheter and the introducer needle are assembled so that the sharp distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e. a smaller blood vessel that is not connected directly to the heart but is one of the branches of the central blood vessels that is directly connected to the heart. In order to verify proper placement of the assembly in the blood vessel, the clinician confirms that there is flashback of blood in the needle and in a flashback chamber located at the proximal end of the needle in conjunction with the needle hub. Once proper placement is confirmed, the clinician applies pressure to the blood vessel by pressing down on the patient's skin distal to the tip of the needle and the catheter. This finger pressure minimizes further blood flow through the catheter and needle. The clinician advances the catheter into the blood vessel, withdraws the needle, leaving the catheter in place, and attaches a fluid handling device to the catheter hub.

Once the introducer needle is withdrawn from the catheter, it is a "blood contaminated sharp" and must be properly handled. With the recognition by the medical device industry of the risk of transmission of Acquired Immunosuppressive Deficiency Syndrome (AIDS) by blood contaminated sharps, various needle shielding mechanisms have been developed. One type of a needle shielding mechanism uses a substantially hollow handle with an introducer needle movably disposed in the handle. In such a device, the sharp distal tip of the needle may be extended from a hollow handle so the sharp distal tip of the needle is exposed. After the needle has been used to place a catheter into a patient, the needle can be retracted into the handle so that the sharp distal tip of the needle is no longer exposed. Various biasing mechanisms can be used to allow the introducer needle to be retracted into the handle after use. For example, a helical spring, either in compression or tension, could be used to provide the biasing force. Alternatively, an elastic tube could be used to provide the biasing force. In order to minimize the number of parts needed for the device, a vacuum created in the proximal portion of the handle between the proximal wall of the handle and the proximal portion of the needle hub can be used to provide the biasing force to retract the needle into the handle since the proximal end of the needle is typically connected to a needle hub. Typically a latching mechanism is used to temporarily lock the needle hub in the extended position for use with the catheter so the sharp distal tip of the needle is distal of the distal end of the handle.

When a vacuum is used to provide the biasing force, the needle hub includes an elastomeric stopper that engages the sidewalls of the handle. This stopper creates an airtight seal between the portion of the handle proximal of the stopper and the portion of the handle distal of the stopper. One side effect of the use of an elastomeric stopper is that the frictional force between the stopper and the sidewall tends to hold the needle hub in place even when the latch is activated to allow the biasing mechanism to bias the needle hub toward the proximal end of the handle. Such an occurrence is unacceptable where the needle retraction mechanism is designed to withdraw the needle into the handle to prevent accidental needle sticks.

SUMMARY OF THE INVENTION

It is an object of this invention to provide a needle retraction mechanism that consistently retracts the needle into the handle.

It is another object of this invention to provide a needle retraction mechanism that includes a latching mechanism that facilitates the retraction of the needle into the handle even where a high coefficient of friction exists between the needle hub and the handle.

The needle retraction mechanism of the present invention includes a hollow handle defining an inner wall, an outer wall and a cavity, a needle, a needle hub and a needle cover. The handle has a closed proximal end and a distal end defining an opening therein. The handle includes a release mechanism adjacent to the distal end. This release mechanism cooperates with the needle hub to hold the needle in the extended position and then to allow the needle to be retracted into the handle after the needle has been used.

The needle has an open bore therethrough with a sharp distal tip and a proximal end. The needle hub assembly is connected to the proximal end of the needle and defines a flashback chamber therein. The needle hub also includes a flexible stopper portion that engages the inner wall of the handle and creates an air tight seal with the inner wall. Since the stopper creates an air tight seal with the inner wall, moving the needle hub distally creates a vacuum in the space between the proximal end of the handle and the needle hub. This vacuum biases the needle hub and thus the needle toward the proximal end of the handle. The stopper and needle hub are configured so the distal portion of the stopper is in communication with the opening in the distal end of the handle. This allows atmospheric pressure to be applied to the distal portion of the stopper.

The needle hub includes a cantilevered arm that engages with a shoulder formed in the inner wall of the handle to hold the needle in the extended position. A tab is formed in the handle adjacent to the shoulder to engage the cantilevered arm and move the cantilevered arm out of engagement with the shoulder. This allows the vacuum created proximal of the stopper to bias the needle hub, and thus the needle, toward the proximal end of the handle. The tab and cantilevered arm are configured so that downward movement of the tab into contact with the cantilevered arm also creates a generally axially directed proximal movement of the needle hub. Such a movement is sufficient to overcome the frictional force holding the stopper to the inner wall of the handle. This movement can be achieved by forming a cam or inclined surface on the tab or the cantilevered arm such that when the tab engages the cantilevered arm, at least a portion of the motion of the tab is converted into a proximally directed motion of the needle hub.

A needle cover is removably connected to the needle hub and is disposed over the needle. The needle cover includes a configuration that is easily grasped by a clinician to facilitate extension of the needle. When the needle retraction mechanism of the present invention is used to place a catheter into a patient, a standard catheter is located coaxially over the needle.

In the retracted position prior to use, the needle hub is adjacent to the proximal end of the handle. The handle is long enough so that the sharp distal tip of the needle does not extend past the distal end of the handle. Indeed preferably, the sharp distal tip of the needle is proximal of the distal end of the handle. This further minimizes the chance of an accidental needle stick from occurring if the needle cover is accidentally removed from the needle prior to use or after the needle has been retracted into the handle after use.

Prior to use of the needle retraction mechansim of this invention, the needle cover is disposed over the needle to shield the sharp distal tip of the needle. In addition, the needle cover is operatively connected to the needle hub with the distal portion of the needle cover extending beyond the distal end of the handle. This provides a handle for the clinician to grasp the needle cover and extend the needle so the sharp distal tip of the needle extends beyond the distal end of the handle. The needle cover becomes disengaged from the needle hub when the needle hub has been extended to the distal position so the sharp distal tip of the needle extends beyond the distal end of the handle. When the clinician properly places the catheter into a patient, the clinician can press the tab of the handle to allow the vacuum to bias the needle hub and thus the needle toward the retracted position.

The above and other objects and advantages of the invention will be apparent upon consideration of the following detailed description.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
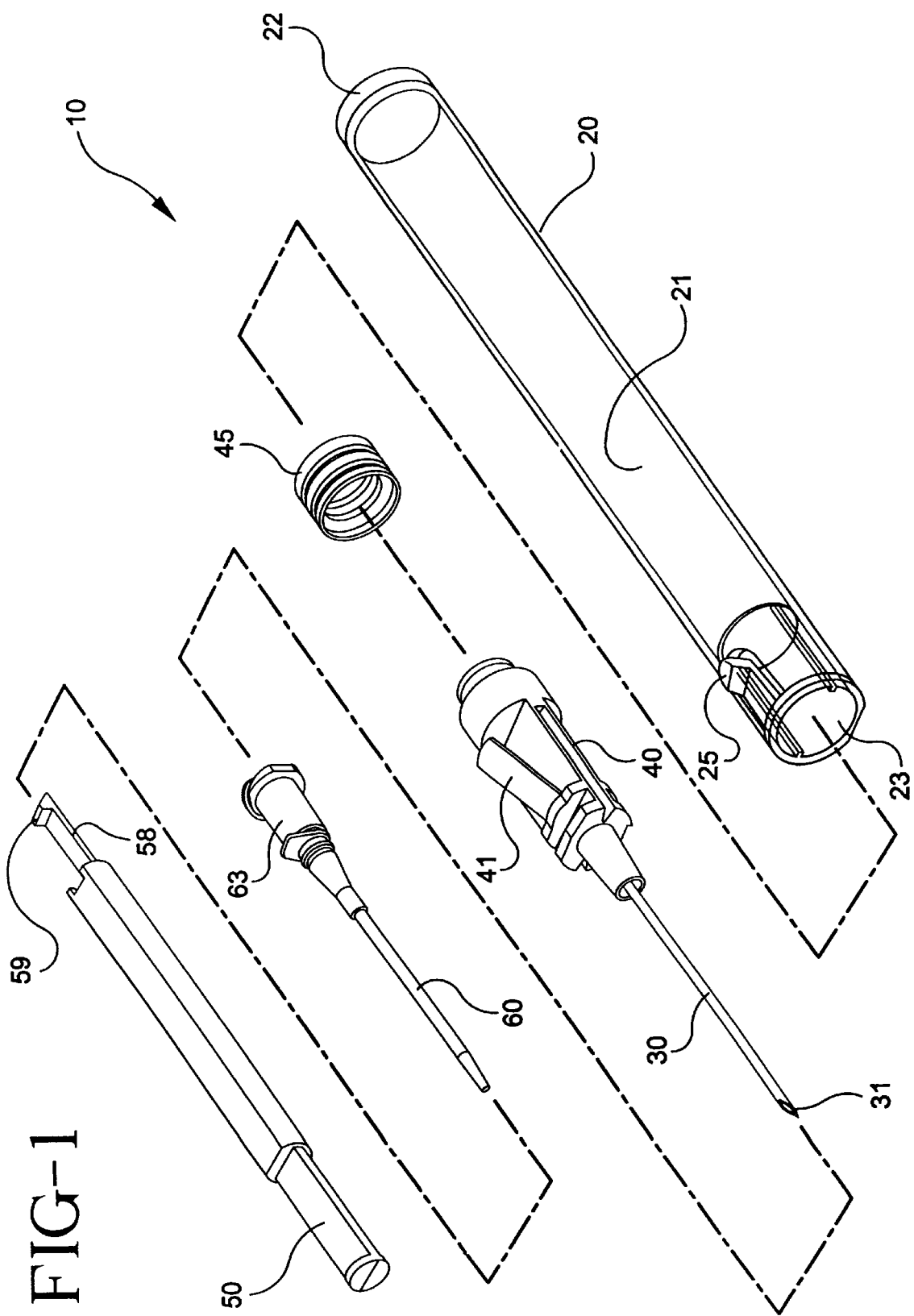
FIG. 1 is an exploded perspective view of the needle retraction mechanism of the present invention in combination with an intravascular catheter.

As used herein, the term "proximal" refers to a location on the needle retraction mechanism of this invention closest to the clinician using the device and farthest from the patient in connection with whom the device is used. Conversely, the term "distal" refers to a location on the needle retraction mechanism of this invention farthest from the clinician using the device and closest to the patient in connection with whom the device is used.

Although this invention is described herein in connection with intravascular catheters, it is to be understood that this invention is applicable to other medical devices where it is desirable for a medical needle to be shielded after use. In addition, while this invention is satisfied by embodiments in many different forms, there are shown in the drawings and herein described in detail, preferred embodiments of the invention with the scope of the invention measured by the appended claims.

Figure 2:
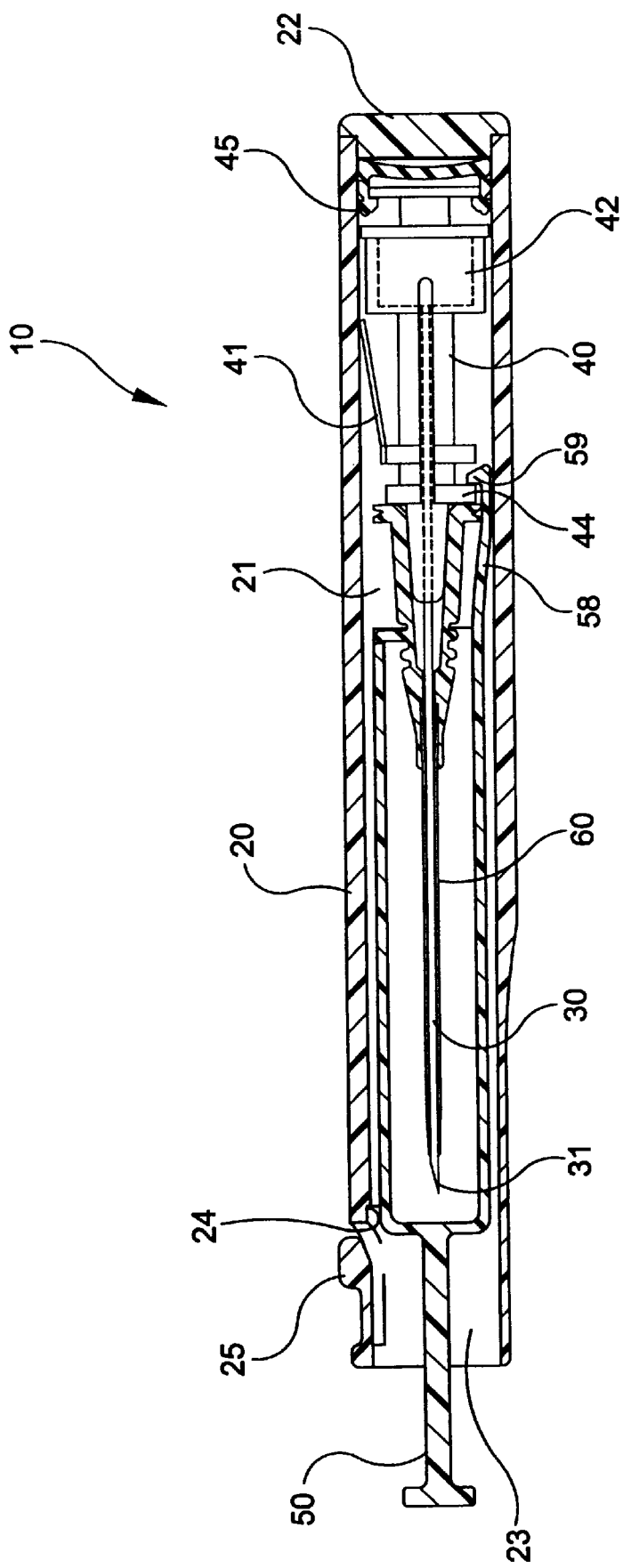
FIG. 2 is a cross-sectional view of the needle retraction mechanism of the present invention in combination with an intravascular catheter with the needle in the retracted position and the needle cover still covering the needle.
Figure 3:
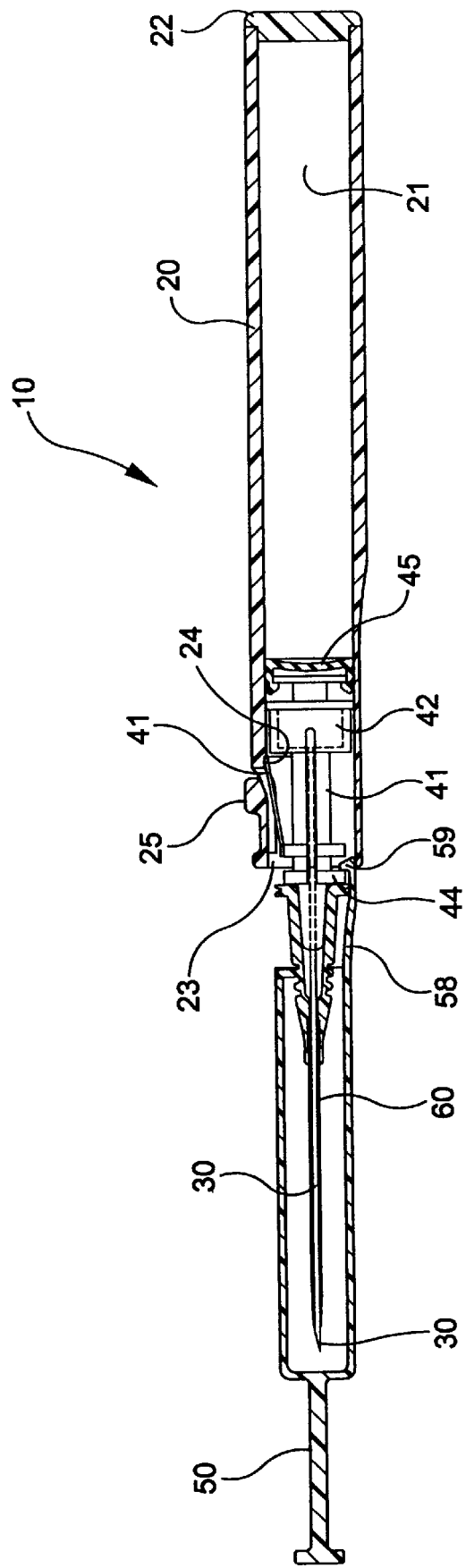
FIG. 3 is a cross-sectional view of the needle retraction mechanism of the present invention in combination with an intravascular catheter with the needle in the extended position and the needle cover still covering the needle.

Referring to the FIG. 1, the needle retraction mechanism 10 of the present invention includes a hollow handle 20, an elongate introducer needle 30, a needle hub assembly 40, a flexible, elastomeric stopper 45 connected to needle hub assembly 40, a needle cover 50 and a catheter 60. No separate biasing element is used in the present invention. Instead a vacuum created proximal of stopper 45, when needle hub assembly 40 is moved from its proximal position in handle 20, see FIG. 2, to its distal position in handle 20, see FIG. 3, is used to bias needle hub assembly 40, and thus needle 30, toward the retracted postion.

Handle 20 defines an elongate cavity 21 and has a closed proximal end 22 and an open distal end 23. Suitable materials for forming handle 20 include, but are not limited to, thermoplastic polymeric resins such as polycarbonate, polystyrene, polypropylene and the like. Handle 20 is preferably formed from a substantially transparent or at least translucent material to allow a clinician to view the interior thereof.

Handle 20 includes a latching mechanism that may be located along a distal portion of handle 20. The latching mechanism temporarily locks needle hub assembly 40 adjacent to distal end 23 of handle 20 against the bias of the vacuum created between stopper 45 and proximal end 22 of handle 20 when stopper 45 is moved distally from its retracted position. See FIG. 5. The latching mechanism can take many forms. See for example U.S. Pat. No. 5,487,734 the disclosure of which is expressly incorporated herein by reference. However, preferably the latching mechanism is a distally facing shoulder 24 formed adjacent to distal end 23 of handle 20. Distally facing shoulder 24 engages an upwardly biased flexible, cantilevered arm 41 movably connected to needle hub assembly 40 to temporily lock needle hub assembly 40 of the needle retraction mechanism of the present invention in the extended position against the bias of the vacuum. A tab 25 formed in and connected to the wall of handle 20 via a living hinge is used to disengage flexible, cantilevered arm 41 from distally facing shoulder 24 to allow needle hub assembly 40, and thus needle 30, to be retracted toward proximal end 22 of handle 20 by the bias of the vacuum.

Figure 5:
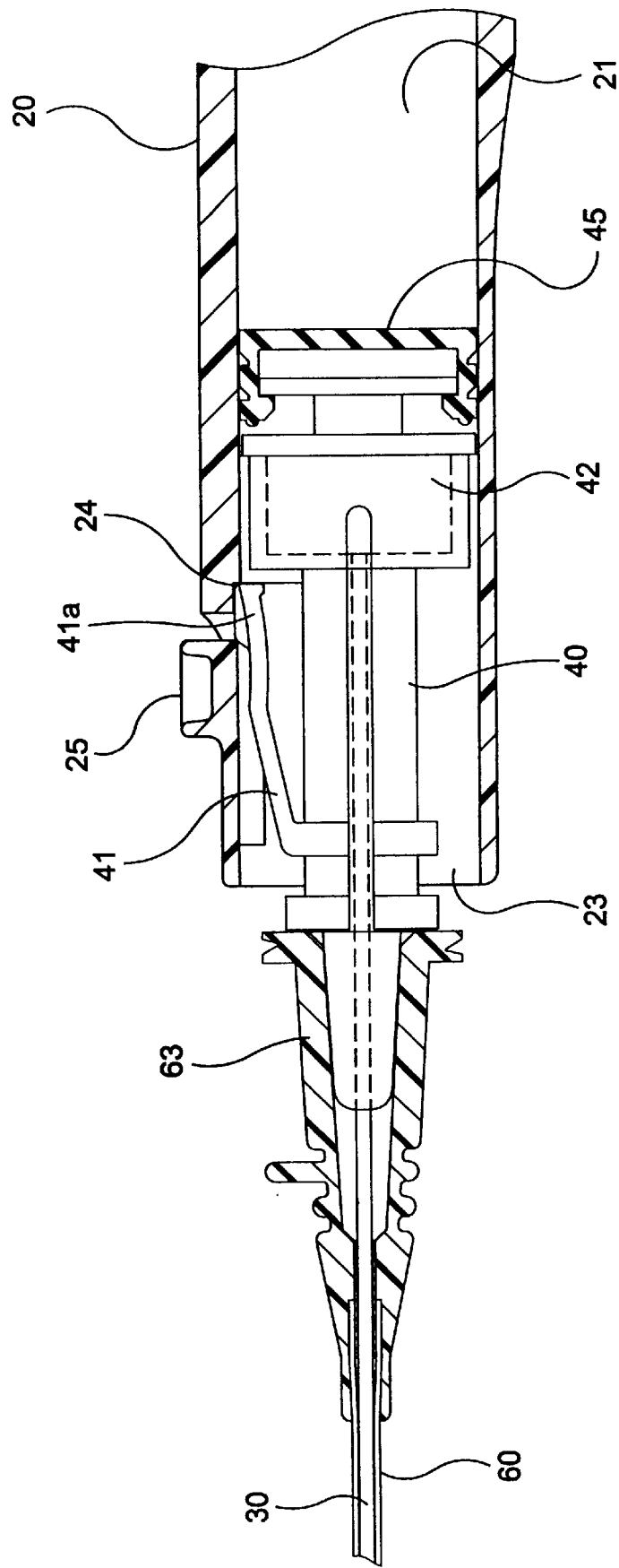
FIG. 5 is an enlarged cross-sectional view of a distal portion of the needle retraction mechanism of the present invention in combination with an intravascular catheter with the needle in the extended position and the needle cover removed.
Figure 6:
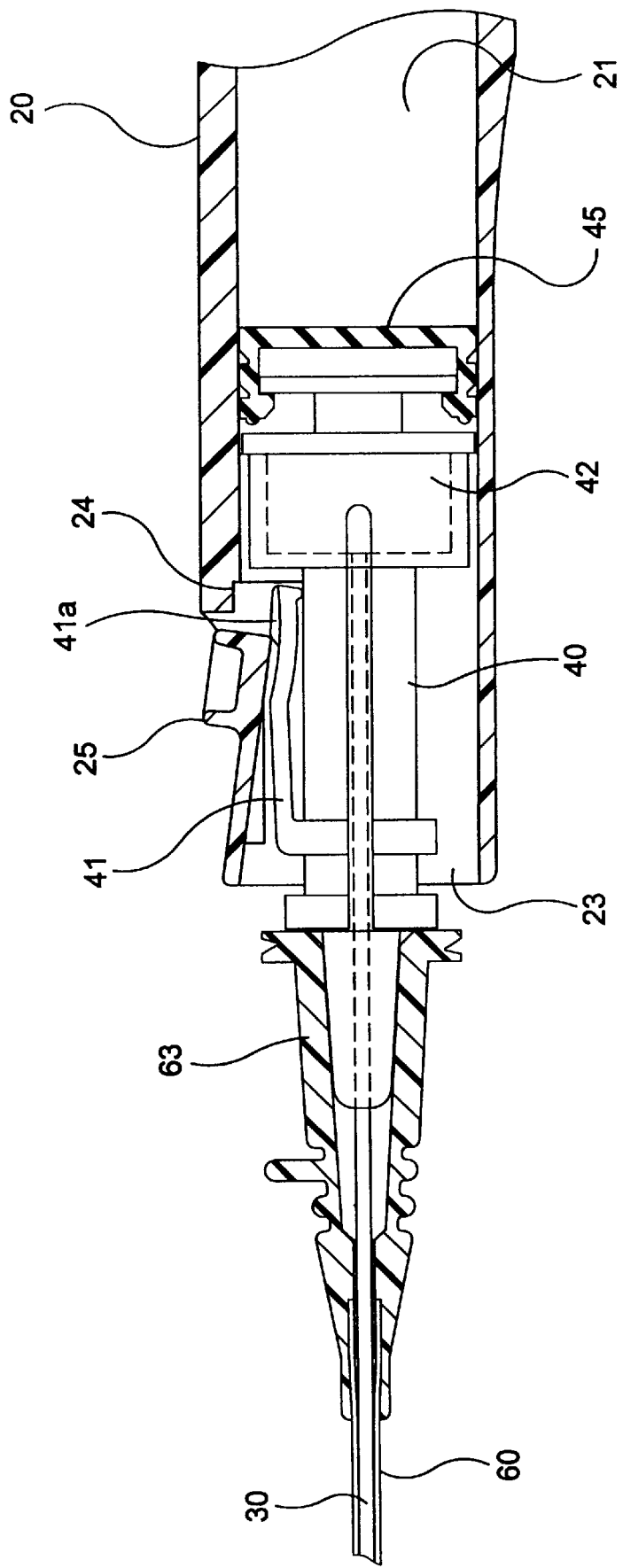
FIG. 6 is an enlarged cross-sectional view of a distal portion of the needle retraction mechanism of the present invention in combination with an intravascular catheter with the latch partially depressed prior to retraction of the needle.
Figure 7:
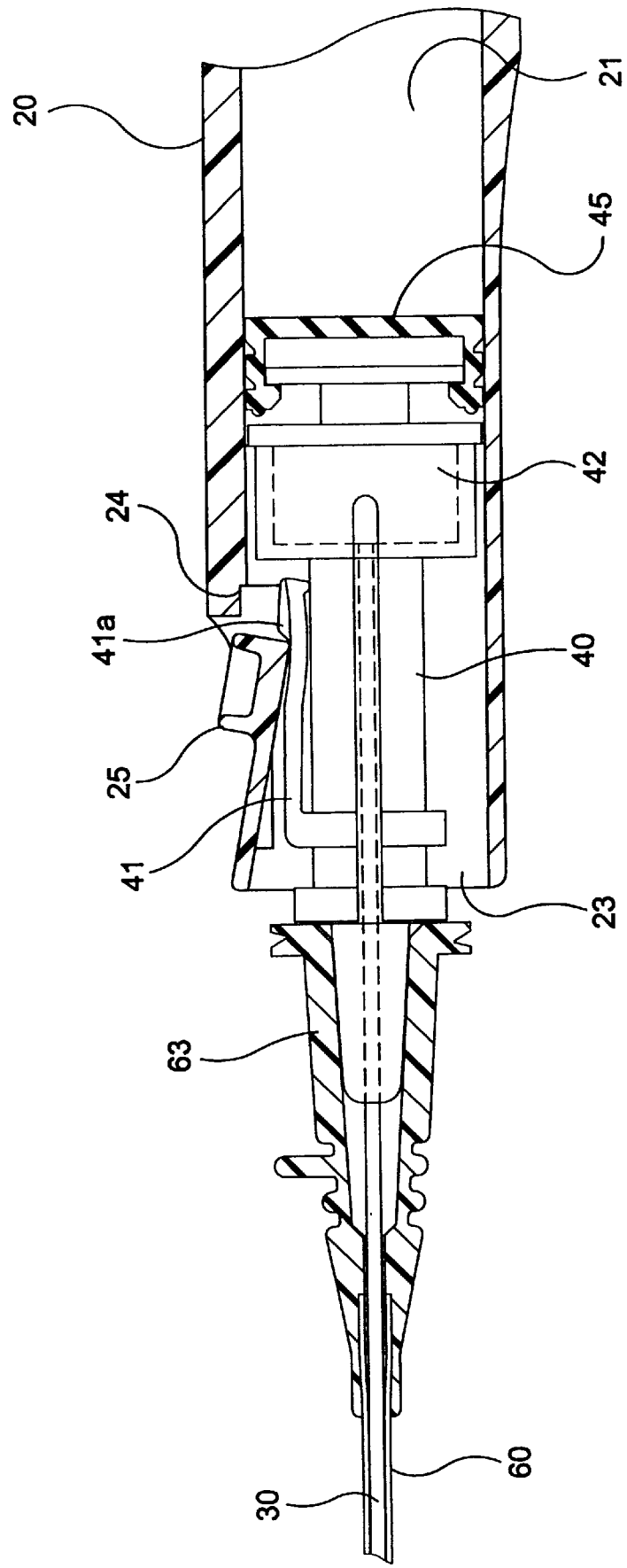
FIG. 7 is an enlarged cross-sectional view of a distal portion of the needle retraction mechanism of the present invention in combination with an intravascular catheter with the latch fully depressed to initiate retraction of the needle.

In one embodiment of this invention, see FIGS. 5–7, arm 41 includes a cam 41a formed on a top proximal portion thereof. Cam 41a includes an angular distal portion. When tab 25 is depressed, a proximal, lower portion of tab 25 engages cam 41a along its angular distal portion. In this manner, at least a portion of the downward motion of tab 25 is translated into a generally axial, proximally directed force that moves needle hub assembly 40 proximally. This axial, proximally directed force helps to initiate needle retraction by overcoming the static frictional force between flexible stopper 45 and the inner wall of handle 20 that may tend to hold flexible stopper 45 against the bias of the vacuum.

Figure 8:
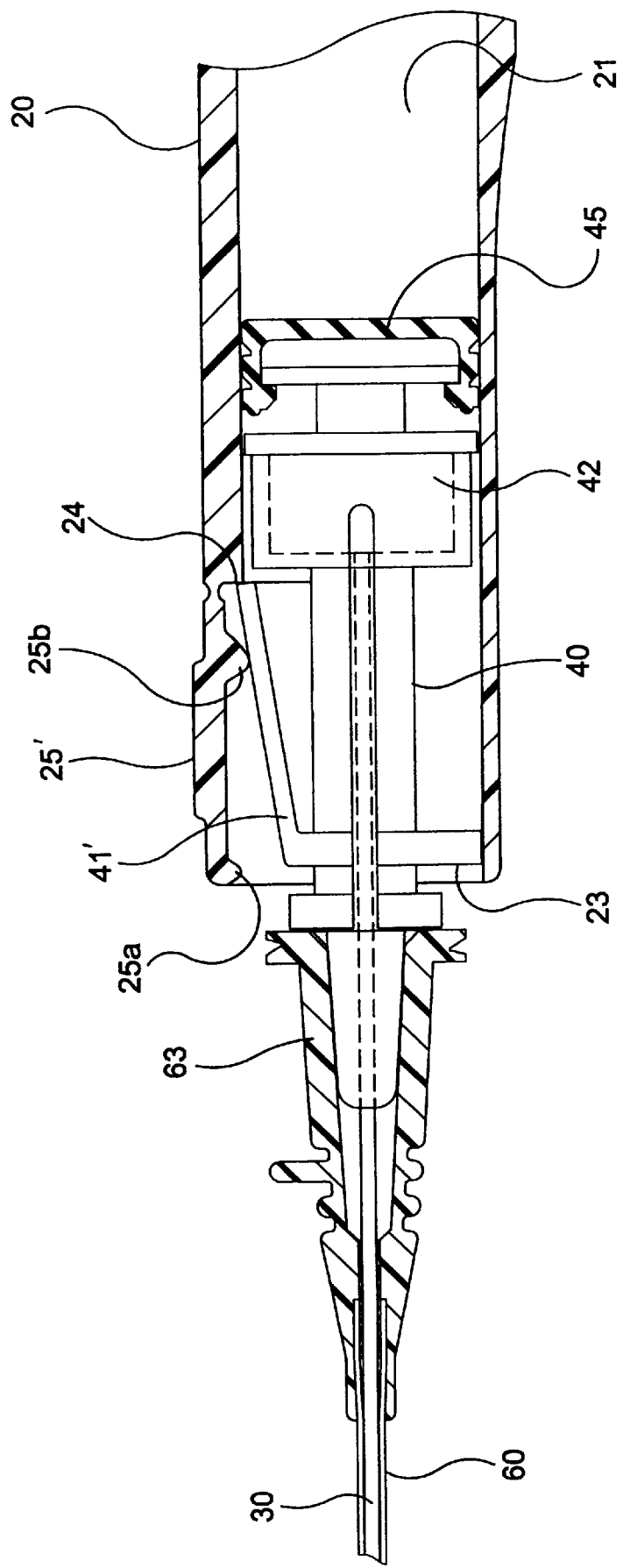
FIG. 8 is an enlarged cross-sectional view of a distal portion of a second embodiment of the needle retraction mechanism of the present invention in combination with an intravascular catheter with the needle in the extended position.
Figure 9:
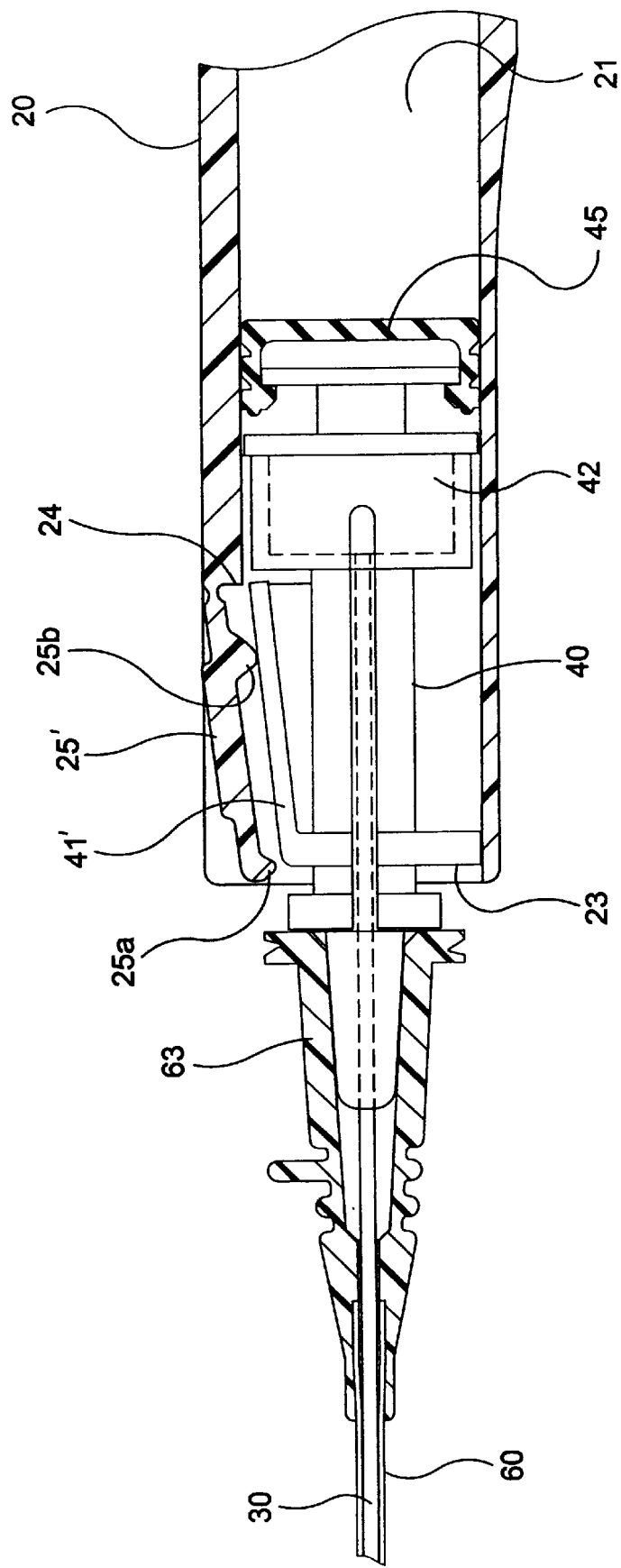
FIG. 9 is an enlarged cross-sectional view of a distal portion of a second embodiment of the needle retraction mechanism of the present invention in combination with an intravascular catheter with the latch partially depressed prior to retraction of the needle.
Figure 10:
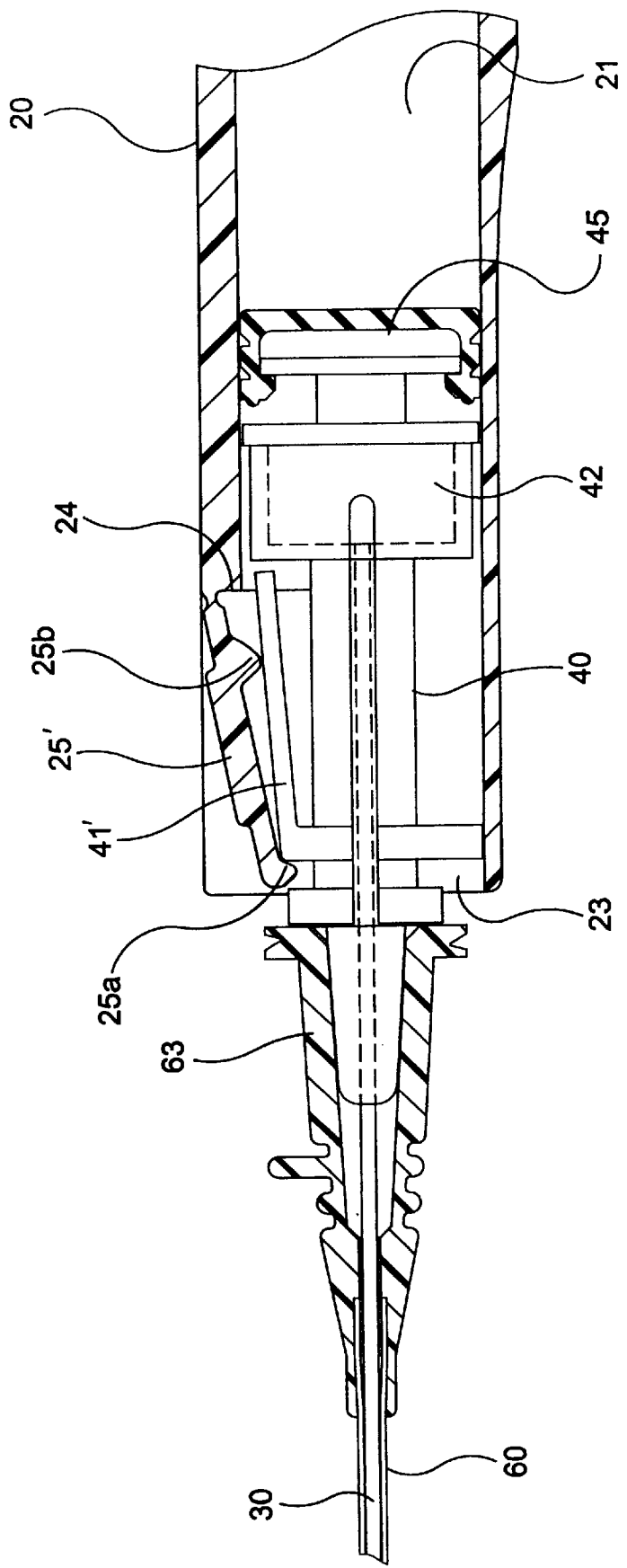
FIG. 10 is an enlarged cross-sectional view of a distal portion of a second embodiment of the needle retraction mechanism of the present invention in combination with an intravascular catheter with the latch fully depressed to initiate retraction of the needle.

In a second embodiment of this invention, see FIGS. 8–10, tab 25' includes a distal cam 25a and a proximal cam 25b. Cams 25a and 25b are located along a bottom portion of tab 25' so as to engage arm 41' upon downward movement of tab 25'. Cam 25b engages arm 41' initially when tab 25' is moved downwardly. See FIG. 8. As tab 25' continues to move downwardly, cam 25a comes into contact with a distal end portion of arm 41'. See FIG. 10. In this manner, at least a portion of the downward motion of tab 25' is translated into a generally axial, proximally directed force that moves needle hub assembly 40 proximally. Again, this axial, proximally directed force helps to initiate needle retraction by overcoming the static frictional force between flexible stopper 45 and the inner wall of handle 20 that may tend to hold flexible stopper 45 against the bias of the vacuum.

Preferably the portion of tab 25 or 25' that engages arm 41 or 41' is rounded in order to minimize friction therebetween. In addition, that portion of arm 41 or 41' that engages tab 25 or 25' is also rounded. For example, a radius of about 0.250 inches is used on the angular distal portion of cam 41a. And the angular distal portion of cam 41a is inclined at an angle of about 45 degrees to arm 41.

Needle 30 typically has an open bore therethrough, although a solid needle could be used, and a sharp distal tip 31 defined by a bevel. Needle 30 is preferably formed from a stainless steel alloy or the like. Needle 30 is connected at its proximal end to needle hub assembly 40.

Needle hub assembly 40 includes flexible, cantilevered arm 41, a flashback chamber 42, and a flexible stopper 45. Except for flexible stopper 45, the greatest diameter of needle hub assembly 40 is less than the inner diameter of handle 20. As noted above, arm 41 engages distally facing shoulder 24 when needle hub assembly 40 is adjacent to distal end 23 of handle 20. Arm 41 is preferably connected to the main body portion of needle hub assembly 40 by a living hinge and is biased away from the main body portion of needle hub assembly 40. As noted above, this allows arm 41 to engage distally facing shoulder 24 when arm 41 is distal of distally facing shoulder 24 and needle hub assembly 40 is biased to proximal end 22 of handle 20. Suitable materials for forming needle hub assembly 40 include, but are not limited to, thermoplastic polymeric resins such as polycarbonate, polystyrene, polypropylene and the like.

As noted above, flexible stopper 45 is connected to the proximal end of needle hub assembly 40. Because the remaining portion of needle hub assembly 40 has a diameter less than the inner diameter of handle 20, the distal face of flexible stopper 45 is exposed to atmospheric pressure. Flexible stopper 45 creates an air tight seal with the inner wall of handle 20. Thus when needle hub assembly 40 is moved from its retracted position adjacent to proximal end 22 of handle 20, see FIG. 2, toward its extended position adjacent to distal end 23 of handle 20, see FIG. 3, a vacuum, or at a minimum an area that is at lower pressure than atmospheric pressure, is created in the space between flexible stopper 45 and proximal end 22 of handle 20. Suitable materials for forming flexible stopper 45 include, but are not limited to, elastomeric thermoset polymers such as polyisoprene and styrene butadiene rubber (SBR).

Preferably, a silicone oil is located in the trough formed in the exterior of flexible stopper 45. This allows flexible stopper 45 to wipe the silicone oil against the inner wall of handle 20 as flexible stopper 45 moves therealong. It has been found that the amount and viscosity of the silicone oil in combination with the degree of interference between flexible stopper 45 and the inner wall of handle 20 affects the retraction speed for needle hub assembly 40 as it is biased toward proximal end 22 by the vacuum. When larger amounts of silicone oil are used, the retraction speed is quicker. When more viscous silicone oil is used, the retraction speed is slower. When the interference is greater, the retraction speed is slower. The degree of interference between flexible stopper 45 and the inner wall of handle 20 also affects the amount of force needed to overcome the static frictional force between flexible stopper 45 and the inner wall of handle 20. The greater the interference, the greater the force needed to overcome the static friction. However, the amount and viscosity of the silicone oil are significantly less relevant.

Needle cover 50 is removably connected to needle hub assembly 40 and is sized and shaped to fit over needle 30 and within handle 20. The purpose of needle cover 50 is two fold. First, needle cover 50 serves to prevent accidental contact with sharp distal tip 31 of needle 30 prior to insertion of needle 30 into a patient. Second, needle cover 50 serves as a handle connected to needle hub assembly 40 to allow a clinician to move needle hub assembly 40 distally to a position adjacent to open distal end 23 of handle 20. When needle hub assembly 40 is in this position it is "armed" and ready for use. Suitable materials for forming needle cover 50 include, but are not limited to, thermoplastic polymeric resins such as polycarbonate, polystyrene, polypropylene and the like.

Figure 4:
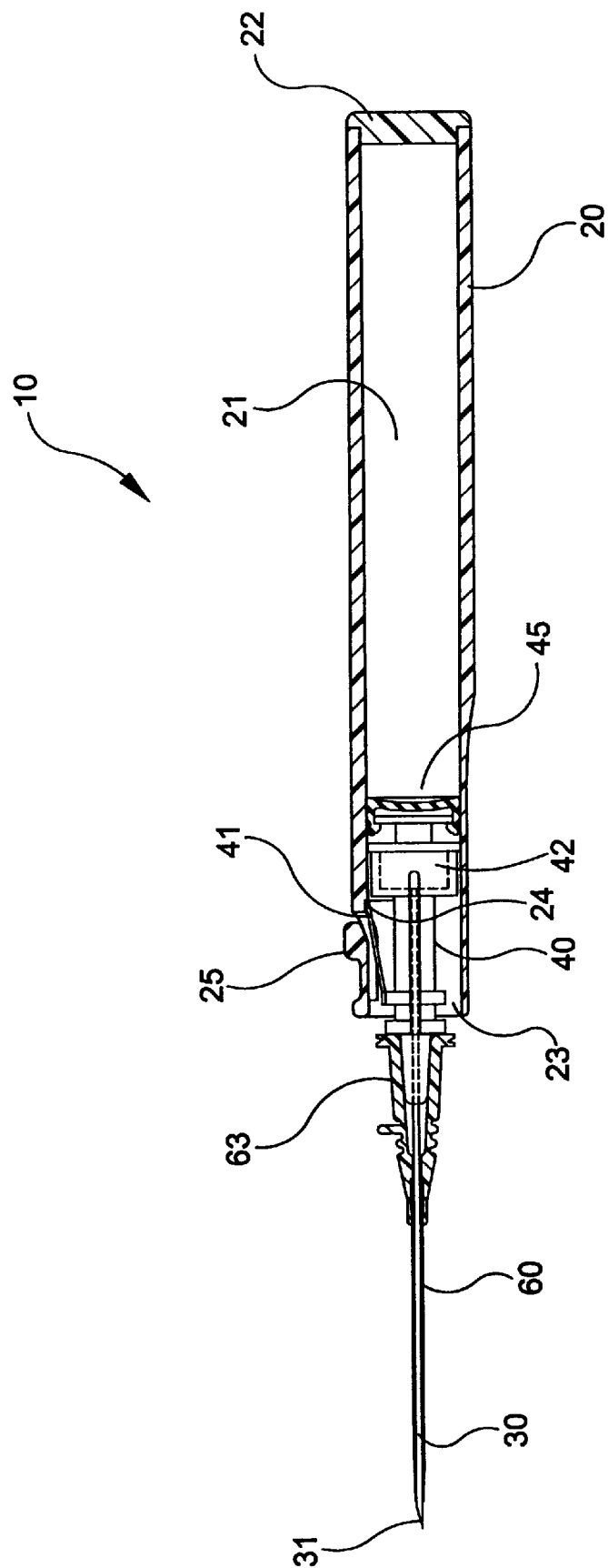
FIG. 4 is a cross-sectional view of the needle retraction mechanism of the present invention in combination with an intravascular catheter with the needle in the extended position and the needle cover removed.

Needle cover 50 should be sufficiently long so that when needle hub assembly 40 is adjacent to proximal end 22, the distal portion of needle cover 50 exends distally beyond distal end 23 of handle 20. See FIG. 2. This makes it easy for the clinician to move needle hub assembly 40 distally. The proximal portion of needle cover 50 is formed with an arm 58 and an upwardly extending finger 59. Finger 59 engages the proximal face of flange 44 and thus pulls needle hub assembly 40 in the distal direction when needle cover 50 is pulled distally. The distal portion of needle hub assembly 40, the distal portion of handle 20, arm 58 and finger 59 must be appropriately configured so that finger 59 will stay engaged with flange 44 until the proximal end of arm 41 is distal of distally facing shoulder 24 but will become disengaged with flange 44 after the proximal end of arm 41 is distal of distally facing shoulder 24. See FIG. 3. Preferably arm 58 is biased outwardly from needle hub assembly 40 so that when the proximal end of arm 41 is distal of distally facing shoulder 24, arm 58 and finger 59 are no longer constrained against outward movement by handle 20. At that point finger 59 will become disengaged from flange 44 and needle hub assembly 40 will be temporarily locked adjacent to distal end 23 of handle 20 by virtue of the engagement between flexible arm 41 and distally facing shoulder 24 against the bias of the vacuum created between proximal end 22 of handle 20 and flexible stopper 45. See FIGS. 4 and 5.

A catheter 60 that has a proximal end, a distal end and a catheter hub 63 affixed to the proximal end of catheter 60 is mounted over needle 30 so that the distal end of catheter 60 is proximal of sharp distal tip 31 of needle 30. Suitable materials for catheter 60 include thermoplastic resins such as fluorinated ethylene propylene (FEP), polyurethane and the like. Preferably, catheter 60 is formed from a thermoplastic hydrophilic polyurethane that softens with exposure to physiological conditions present in the patient's body. Suitable materials for catheter hub 63 include, but are not limited to, thermoplastic polymeric resins such as polycarbonate, polystyrene, polypropylene and the like.

In order to place a catheter into a patient's blood vessel, the clinician grasps the distal portion of needle cover 50 and pulls it so as to move needle hub assembly 40 toward distal end 23 of needle 20. When the proximal end of arm 41 is distal of distally facing shoulder 24, finger 59 becomes disengaged from flange 44 so that needle cover 50 no longer shields needle 30. At this point, the proximal end of arm 41 engages distally facing shoulder 24 to temporarily lock needle hub assembly 40 adjacent to distal end 23 of handle 20 so sharp distal tip 31 of needle 30 and catheter 60 extend beyond distal end 23 of handle 20. See FIG. 4. This distal movement of flexible stopper 45 with needle hub assembly 40 creates a vacuum in the space between proximal end 22 of handle 20 and flexible stopper 45. The clinician can then substantially longitudinally align needle 30 and catheter 50 with the target blood vessel. The bevel of needle 30 should be facing substantially away from the skin surface during venipuncture. The clinician inserts needle 30 and catheter 60 at a shallow angle, preferably less than about 35 degrees, into the skin so that sharp distal tip 31 enters the target blood vessel. The clinician then preferably observes a blood flashback in flashback chamber 42.

After confirming placement of needle 30 and catheter 60 in the target blood vessel, the clinician advances catheter 60 distally axially along needle 30 into position in the blood vessel. After proper placement of catheter 60 is achieved, the clinician places a finger from his other hand on the patient's skin over the blood vessel distal of the distal end of catheter 60 and sharp distal tip 31 of needle 30. By placing his finger on the patient's skin and applying sufficient pressure on the skin, the clinican thereby minimizes blood flow through catheter 60. The clinican then withdraws needle 30 from catheter 60 by depressing tab 25. Depressing tab 25 forces arm 41 toward needle hub assembly 40 and out of engagement with distally facing shoulder 24. This allows the vacuum to urge needle hub assembly 40, and thus needle 30, into the retracted position within needle 20. The clinician may then attach any desired fluid handling device to catheter hub 63 and commence the planned treatment. Handle 20 with needle 30 substantially within it may then be disposed of according to the facility's disposal protocol.

Thus it is seen that a needle retraction mechanism is provided that consistently retracts the needle into the handle and that includes a latching mechanism that facilitates the retraction of the needle into the handle even where a high coefficient of friction exists between the needle hub and the handle.

We claim:

1. A needle retraction device, comprising:
   a handle;
   a tab associated with the handle;
   a needle with a proximal end and a sharp distal point;
   a needle hub connected to the needle and having a proximal portion and a distal portion, the needle hub being movably disposed in the needle hub;
   a biasing mechanism disposed in the handle to move the needle hub from an extended position to a retracted position;
   an arm associated with the needle hub to releasably hold the needle in the extended position; and
   a cam surface on the arm adapted for engagement with the tab such that at least a portion of the downward movement by the tab against the cam surface is translated into a proximally directed axial movement of the needle hub.

2. The needle retraction device of claim 1 wherein the cam surface is defined by an angled distally directed face.

3. The needle retraction device of claim 2 wherein the angled distally directed face is at an angle of about 45 degrees to the arm.

4. A needle retraction device, comprising:
   a handle;
   a tab associated with the handle;
   a first cam associated with the tab;
   a needle with a proximal end and a sharp distal point;
   a needle hub connected to the needle and having a proximal portion and a distal portion, the needle hub being movably disposed in the needle hub;
   a biasing mechanism disposed in the handle to move the needle hub from an extended position to a retracted position; and
   an arm associated with the needle hub to releasably hold the needle in the extended position wherein downward movement of the tab causes the first cam to engage the arm and translate at least a portion of the downward movement into a proximally directed axial movement of the needle hub.

5. The medical device of claim 4 wherein the first cam is located along a lower portion of the tab.

6. The medical device of claim 4 further comprising a second cam associated with the tab.

7. The medical device of claim 5 wherein the first cam and the second cam are located along a lower portion of the tab.

8. A needle retraction device, comprising:
   a handle;
   a needle with a proximal end and a sharp distal point;
   a needle hub connected to the needle and having a proximal portion and a distal portion, wherein the needle hub is movably disposed in the handle;
   a biasing mechanism disposed in the handle to move the needle hub from an extended position to a retracted position;
   a means for releasably holding the needle in an extended position; and
   a means for contacting the means for releasably holding the needle in an extended position wherein at least a portion of the movement of the means for contacting is translated into a proximally directed axial movement of the needle hub.

* * * * *